US010328280B2

United States Patent
Stopek

(10) Patent No.: US 10,328,280 B2
(45) Date of Patent: *Jun. 25, 2019

(54) SYSTEM AND METHOD FOR LUNG DENERVATION

(71) Applicant: Covidien LP, Mansfield, MA (US)

(72) Inventor: Joshua B. Stopek, St. Louis Park, MN (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/175,135

(22) Filed: Feb. 7, 2014

(65) Prior Publication Data

US 2014/0228614 A1    Aug. 14, 2014

Related U.S. Application Data

(60) Provisional application No. 61/762,741, filed on Feb. 8, 2013, provisional application No. 61/936,933, filed on Feb. 7, 2014.

(51) Int. Cl.
| | | |
|---|---|---|
| *A61N 5/10* | (2006.01) | |
| *A61B 34/10* | (2016.01) | |
| *A61B 90/00* | (2016.01) | |

(52) U.S. Cl.
CPC ............ *A61N 5/1039* (2013.01); *A61B 34/10* (2016.02); *A61B 90/37* (2016.02); *A61N 5/1049* (2013.01); *A61N 5/1068* (2013.01); *A61N 2005/1051* (2013.01); *A61N 2005/1055* (2013.01); *A61N 2005/1058* (2013.01)

(58) Field of Classification Search
None
See application file for complete search history.

(56) References Cited

U.S. PATENT DOCUMENTS

| | | | | |
|---|---|---|---|---|
| 5,217,456 A | * | 6/1993 | Narciso, Jr. ........ | A61B 1/00177 606/15 |
| 5,553,618 A | * | 9/1996 | Suzuki ..................... | A61N 7/02 600/411 |
| 5,754,623 A | | 5/1998 | Seki | |
| 5,845,636 A | | 12/1998 | Gruenke et al. | |
| 6,188,355 B1 | * | 2/2001 | Gilboa .................. | G01S 5/0205 324/207.17 |

(Continued)

FOREIGN PATENT DOCUMENTS

| | | |
|---|---|---|
| CN | 1627324 A | 6/2005 |
| JP | 2005514969 A | 5/2005 |

(Continued)

OTHER PUBLICATIONS

Supplementary European Search Report for EP 14 74 9591 dated Aug. 12, 2016.

(Continued)

*Primary Examiner* — Carolyn A Pehlke

(57) ABSTRACT

Systems and methods for treating a lung disease including capturing a first set of images of at least a portion of a lung displaying symptoms of a lung disease, generating a three dimensional model from the first set of images, locating a target nerve proximate the portion of the lung, generating a treatment plan, and on-invasively denervating the target nerve based on the treatment plan such that the function of the portion of the lung is affected.

20 Claims, 9 Drawing Sheets

(56) References Cited

U.S. PATENT DOCUMENTS

| | | | |
|---|---|---|---|
| 6,226,543 B1 * | 5/2001 | Gilboa | A61B 5/06 378/98.8 |
| 6,634,363 B1 | 10/2003 | Danek et al. | |
| 7,027,869 B2 | 4/2006 | Danek et al. | |
| 7,517,320 B2 | 4/2009 | Wibowo et al. | |
| 7,542,802 B2 | 6/2009 | Danek et al. | |
| 7,594,925 B2 | 9/2009 | Danek et al. | |
| 7,708,768 B2 | 5/2010 | Danek et al. | |
| 7,740,017 B2 | 6/2010 | Danek et al. | |
| 8,161,978 B2 | 4/2012 | Danek et al. | |
| 8,218,846 B2 | 7/2012 | Trumer et al. | |
| 8,235,983 B2 | 8/2012 | Webster et al. | |
| 8,292,882 B2 | 10/2012 | Danek et al. | |
| 8,459,268 B2 | 6/2013 | Danek et al. | |
| 8,640,711 B2 | 2/2014 | Danek et al. | |
| 2005/0203420 A1 * | 9/2005 | Kleen | A61B 5/0071 600/476 |
| 2006/0247683 A1 * | 11/2006 | Danek | A61N 1/378 607/2 |
| 2007/0265521 A1 * | 11/2007 | Redel | A61B 5/0066 600/411 |
| 2009/0306644 A1 * | 12/2009 | Mayse | A61B 8/12 606/33 |
| 2010/0008555 A1 | 1/2010 | Trumer et al. | |
| 2011/0118725 A1 * | 5/2011 | Mayse | A61B 18/02 606/33 |
| 2011/0249880 A1 * | 10/2011 | Parikh | A61B 5/06 382/131 |
| 2011/0301587 A1 | 12/2011 | Deem et al. | |
| 2012/0172871 A1 * | 7/2012 | Hastings | A61B 8/0891 606/41 |
| 2012/0245494 A1 | 9/2012 | Gertner | |
| 2012/0249546 A1 | 10/2012 | Tschirren et al. | |
| 2012/0294424 A1 | 11/2012 | Chin et al. | |

FOREIGN PATENT DOCUMENTS

| | | | | |
|---|---|---|---|---|
| JP | 2012-210232 A | 11/2012 | | |
| JP | 2013507198 A | 3/2013 | | |
| WO | 2009/074872 A2 | 6/2009 | | |
| WO | 2009/137819 A1 | 11/2009 | | |
| WO | WO 2011060200 A1 * | 5/2011 | | A61B 18/1492 |
| WO | 2013011733 A1 | 1/2013 | | |

OTHER PUBLICATIONS

Giraud P et al., "Reduction of organ motion effects in IMRT and conformal 3D radiation delivery by using gating and tracking techniques", Cancer Radiotherapie, vol. 10, No. 5, pp. 269-282 (2006).

Chinese Office Action issued in corresponding Application No. CN201480009021.8, dated Nov. 9, 2016, 18 pages.

Second Office Action issued in corresponding Chinese application No. 201480009021.8 dated Jul. 18, 2017.

Examination Report issued in corresponding Australian application No. 2014214766 dated Jul. 25, 2017.

Japanese Office Action issued in Japanese Patent Application No. 2015-557114, dated Apr. 17, 2018.

Japanese Office Action issued in Japanese Patent Application No. 2015-557114, dated Dec. 12, 2017.

Third Office Action issued in corresponding Chinese application No. 201480009021.8 dated Feb. 23, 2018.

International Search Report issued in corresponding Appl. No. PCT/US14/15281 dated Apr. 30, 2014 (1 page).

* cited by examiner

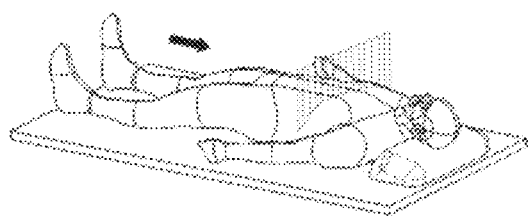
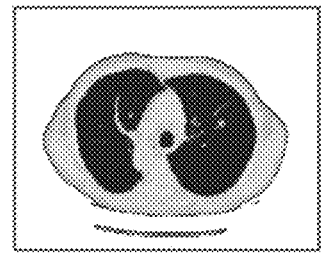
FIG. 2A　　　　　　　　　　　FIG. 2B
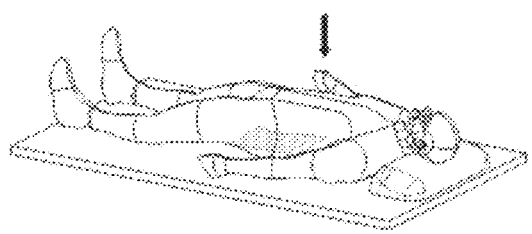
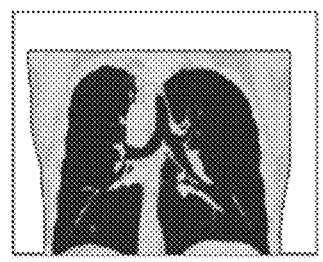
FIG. 2C　　　　　　　　　　　FIG. 2D
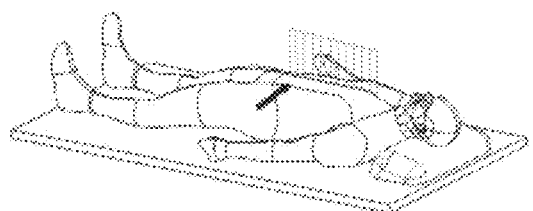
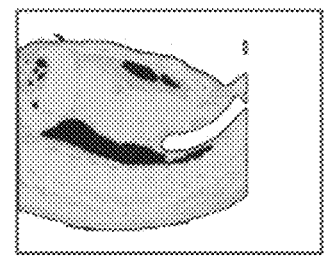
FIG. 2E　　　　　　　　　　　FIG. 2F

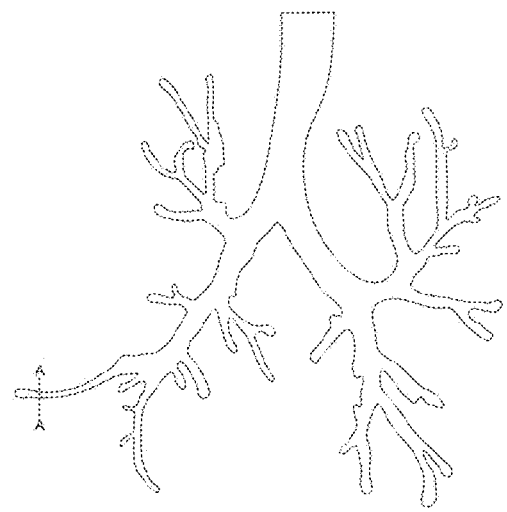
FIG. 5A
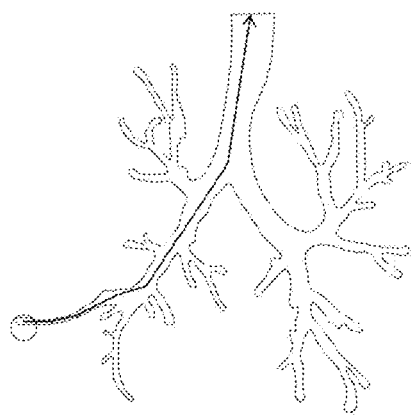 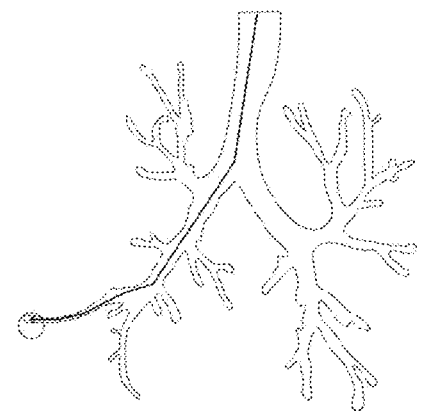
FIG. 5B   FIG. 5C

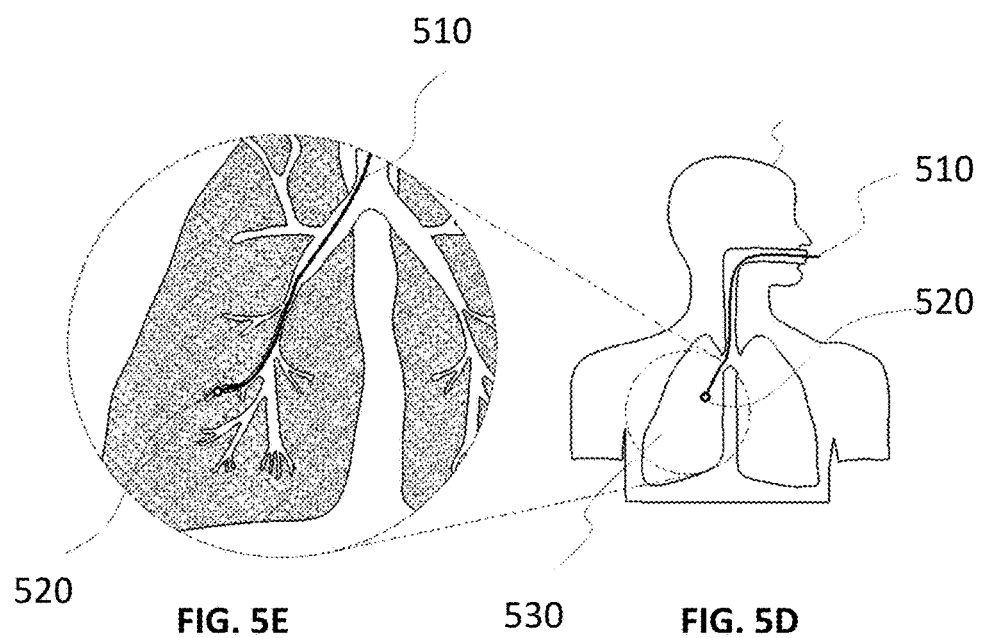
FIG. 5E  FIG. 5D

SYSTEM AND METHOD FOR LUNG DENERVATION

CROSS REFERENCE TO RELATED APPLICATIONS

The present application claims the benefit of and priority to U.S. Provisional Patent Application Ser. No. 61/762,741 filed on Feb. 8, 2013, and U.S. Provisional Patent Application Ser. No. 61/936,933 filed on Feb. 7, 2014, the entire contents of which are incorporated herein by reference.

BACKGROUND

Technical Field

The present disclosure relates to systems and methods for treating lung diseases. More particularly, the present disclosure relates to systems and methods that identify one or more target nerves of a lung and treats the target nerves non-invasively based on a three dimensional model of the lung.

Discussion of Related Art

Standard of care for lung diseases, such as asthma, chronic obstructive pulmonary disease (COPD), and chronic obstructive lung disease (COLD), or for lung-related diseases, such as emphysema, chronic bronchitis, gastro esophageal reflux, cardiovascular disease, and rhinosinusitis, has been focused largely on medical and/or drug management which are highly invasive to patients in general. For example, it has been reported for decades that lung denervation via localized and invasive means (e.g., surgery) may provide therapeutic benefit for asthma or emphysema.

Poor airflow generally results in breakdown of lung which causes lung diseases. Sometimes, walls of alveoli are damaged and, in result, air is trapped inside of the damaged alveoli of the lung so that amount air during inhalation and exhalation decreases and symptoms of lung diseases increase. One way to treat damaged alveoli may be denervation of a nerve so as to disable whole or parts of functions of the nerve that affects contraction of the damaged alveoli. Some medical devices have been developed to denervate nerves by inserting an ablation device to the target. For a variety of reasons, including the infirmity of pulmonary patients, and technical challenges the adoption of such devices for denervation has been relatively weak. The present disclosure provides an alternative methodology for treatment which may be applicable to a broader range of patients.

SUMMARY

In an aspect, the present disclosure features a method for treating a lung disease. The method includes capturing a first set of images of at least a portion of a lung displaying symptoms of a lung disease, generating a three dimensional model from the first set of images, locating a target nerve proximate the portion of the lung, generating a treatment plan, and non-invasively denervating the target nerve based on the treatment plan such that the function of the portion of the lung is affected.

In an aspect, the treatment plan includes one or more of a treatment size, a treatment vector, a nerve location, an amount of energy, or a treatment period. The treatment size is calculated based on one or more of the severity of the symptoms of the lung disease, a location of the target nerve, a size of the target nerve, and whether the denervation is to be temporary or permanent. Non-invasively denervating the target nerve includes radiating the amount of energy to the target nerve for the treatment period.

In an aspect, the method further includes determining an initiation time to start denervating the target nerve during a breathing cycle of a patient. The initiation time is the time when the target nerve moves the least during the breathing cycle. The treatment time is a period from a time when the patient has substantially completed inhalation to a time when the patient starts exhalation, a period from a time when the patient has substantially completed exhalation to a time when the patient starts inhalation, or a period while the patient holds a breath. The method further includes a plurality of treatment periods until the nerve has been radiated with the amount of energy of the treatment plan.

In an aspect, non-invasively denervating the target nerve includes generating a breathing model for the patient and compensating for the movement of the target nerve based on the breathing model during denervation. Compensating for the movement of the target nerve includes compensating for respiratory movement, cardiac motion, and movement of a patient.

In an aspect, generating the breathing model includes locating the patient on a treatment bed and placing a movement tracking sensor on the patient to monitor movement of the patient with respect to the treatment bed during the patient's breathing cycle. The breathing model is based on the movement of the movement tracking sensor during the patient's breathing cycle.

In an aspect, the three dimensional model is generated from the first set of images captured by one or more imaging device selected from the group consisting of a computed tomography (CT), magnetic resonance imaging (MRI), and an ultrasound imaging device.

In an aspect, the method further includes generating enhanced images which are taken by one or more imaging device selected from the group consisting of tissue spectroscopy, optical coherence tomography, confocal microendoscopy, and fluorescence microendoscopy.

In an aspect, generation of enhanced images includes determining a pathway for the portion of the lung based on the three dimensional model and the images, inserting an ultrasound device into the lungs of the patient following the pathway, and imaging at least the portion of the lung displaying symptoms of the lung disease. The method further includes placing one or more fiducial markers proximate the portion of the lung imaged with the ultrasound device, obtaining a second image set of images of at least a portion of a lung displaying symptoms of a lung disease and combining the ultrasound images with the second set of images, and identifying the target nerve for denervation based on the combined images. The one or more fiducial markers enable registration of the ultrasound images and the second set of images.

In an aspect, the method further includes employing a fluorescent marker to mark the target nerve prior to capturing the first set of images.

In an aspect, non-invasively denervating the target nerve includes placing the patient on a treatment bed and capturing additional images to register a location of the target nerve with respect to the treatment bed for non-invasive treatment.

Any of the above aspects and embodiments of the present disclosure may be combined without departing from the scope of the present disclosure.

BRIEF DESCRIPTION OF THE DRAWINGS

Objects and features of the presently disclosed systems and methods will become apparent to those of ordinary skill in the art when descriptions of various embodiments are read with reference to the accompanying drawings, of which:

FIG. 2A is a view of a computed tomography (CT) scan image of a patient's lungs taken from the transverse plane in accordance with an embodiment of the present disclosure;

FIG. 2B is perspective view a patient's body illustrating the transverse plane in accordance with an embodiment of the present disclosure;

FIG. 2C is a view of a CT scan image of a patient's lungs taken from the coronal plane in accordance with an embodiment of the present disclosure;

FIG. 2D is perspective view of a patient's body illustrating the coronal plane in accordance with an embodiment of the present disclosure;

FIG. 2E is a view of a CT scan image of a patient's lungs taken from the sagittal plane in accordance with an embodiment of the present disclosure;

FIG. 2F is perspective view of a patient's body illustrating the sagittal plane in accordance with an embodiment of the present disclosure;

FIG. 5A is an two dimensional illustration of the lung of FIG. 3;

FIG. 5B is an illustration of finding a pathway from a target to an entry point of a patient in accordance with an embodiment of the present disclosure;

FIG. 5C is an illustration of navigating the pathway of FIG. 5B from the entry point to the target in accordance with an embodiment of the present disclosure;

FIG. 5D is an illustration of an imaging device inserted into the lung following the pathway;

FIG. 5E is an enlarged detail view of the circled area 530 of FIG. 5D;

DETAILED DESCRIPTION

The present disclosure is related to systems and methods for treating lung diseases using images of the lung to identify and locate a target nerve for denervation treatment. One or more imaging modalities may be used to provide sufficient resolution to locate the target nerve. Treatments are performed from outside of a patient's body and thus are not invasive to the patient.

Although the present disclosure will be described in terms of specific illustrative embodiments, it will be readily apparent to those skilled in this art that various modifications, rearrangements and substitutions may be made without departing from the spirit of the present disclosure. The scope of the present disclosure is defined by the claims appended hereto.

Figure 1:
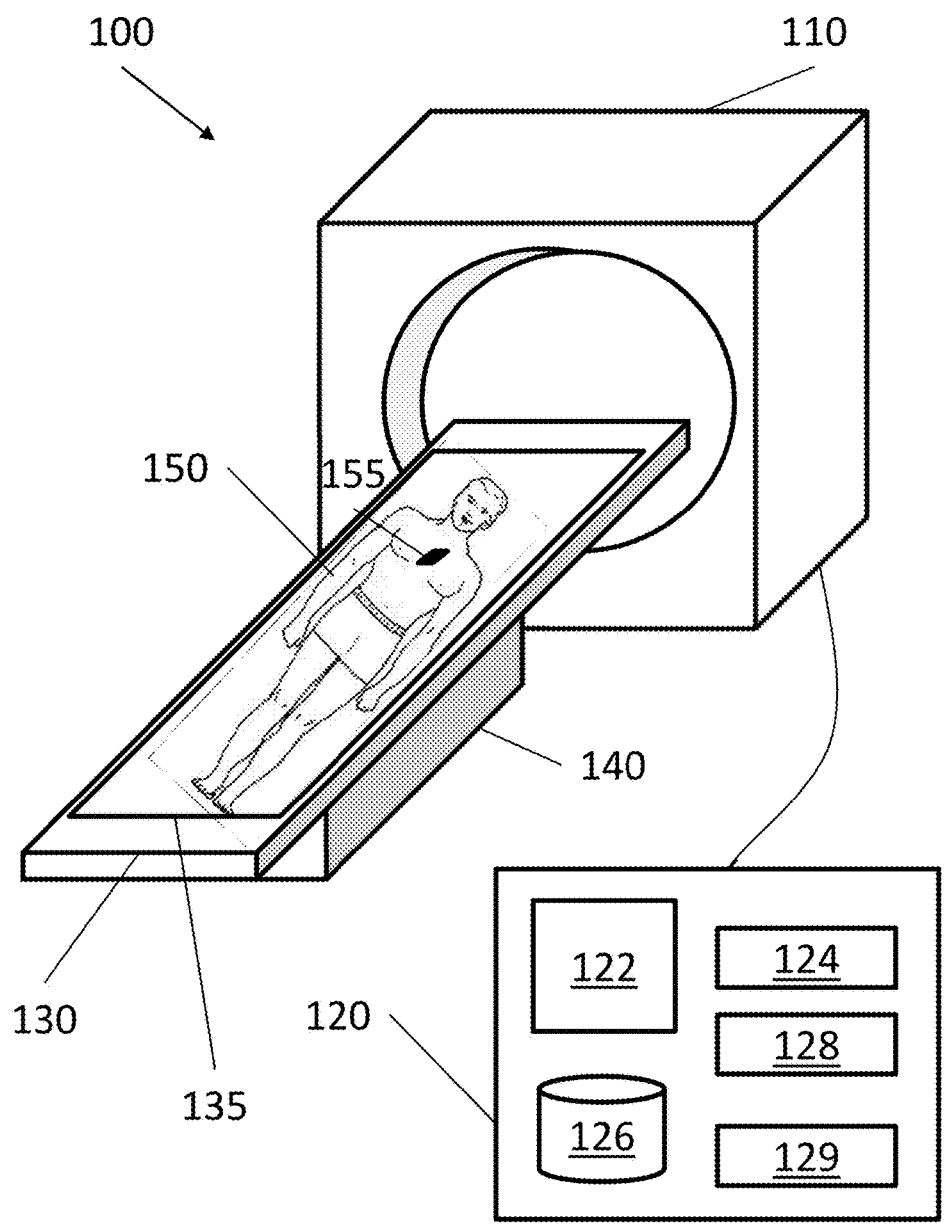
FIG. 1 is a perspective view of a system for treating lung diseases of a patient in accordance with an embodiment of the present disclosure.

FIG. 1 shows a system 100 that is generally directed to treating lung diseases by denervation. The system includes a treatment device 110, a treatment board 120, a support 130, and a computing device 140. The treatment device 110 may use radiation technique, such as stereotactic body radiation therapy (SBRT), to non-invasively treat a portion of a lung from outside of the patient's body. In embodiments, the treatment device 110 may use other forms of medical techniques or energy, such as high intensity focused ultrasound (HIFU), proton therapy, and others suitable for non-invasive treatment for lung diseases known to those of skill in the art.

In particular, the system 100 non-invasively treats the lung diseases by utilizing a three dimensional model of a lung to identify and locate a target for denervation. The system 100 includes a treatment device 110, a computing device 120, a treatment bed 130, and a support 140. A patient 150 is lying on the treatment bed 130, awaiting entry into the treatment device 110.

As noted above, the treatment device 110 is preferentially of the type which enables treatment of the patient 150, and particularly the lungs of the patient 150 in a non-invasive fashion. In other words, the treatment device 110 radiates treatment energy and focuses the treatment energy on the target. Thus, no incision of the tissue of the patient 150 and no insertion of catheter through a body opening, such as mouth, nose, or medical incision of the body, are necessary for treatment.

In some instances, the treatment device 110 may also be used as an imaging device in accordance with an embodiment of the present disclosure. It has been reported that such devices featuring combined imaging and treatment experience fewer exporting errors, which are generally caused by exporting image data from an imaging device to a treatment device, and may be reduced and localization errors, which are generally caused by different location of a patient between an imaging device and a treatment device. Further, it may be possible to conduct treatment immediately after or even while imaging a portion of the patient 150 (e.g., the lungs).

The treatment device 110 may also be used for repeated or follow-up procedures. For example, in some situations, once a denervation treatment for one or more nerves has been done, the treated nerves are not completely severed and may regenerate. This incomplete severing of the nerve may be part of the treatment plan, or may be an unintended. For this reason, repeated or follow-up treatments may be made to provide additional treatments to the previously treated nerves to either obtain or to maintain the intended therapeutic effect.

The computing device 120, such as, a laptop, desktop, tablet, or other similar computing device, includes a display 122, one or more processors 124, memory 126, a network card 128, and an input device 129. The system 100 may also include multiple computing devices 120, wherein separate computing devices 120 are employed for procedure planning and treatment. The display 122 may be touch-sensitive and/or voice-activated, enabling the display 122 to serve as both an input and output device. The display 122 may display a two dimensional or three dimensional model of a lung to locate and identify a portion of the lung that displays symptoms of the lung diseases. The display 122 may further display options to select, add, and remove a target to be treated and settable items for the treatments.

The one or more processors 124 execute computer-executable instructions. The processors 124 may perform image-processing functions so that the two dimensional or three dimensional model of the lung can be displayed on the display 122. In embodiments, the computing device 120 may further include a separate graphic accelerator that performs only the image-processing functions so that the one or more processors 124 may be available for other programs.

The memory 126 stores data and programs. For example, data may be image data for a two or three dimensional model or any other related data such as patients' medical records, prescriptions and/or history of the patient's diseases. The memory 126 may include one or more solid-state storage devices such as flash memory chips, mass storage, tape drive, or any computer-readable storage medium which is connected to a processor through a storage controller and a communications bus. Computer readable storage media include non-transitory, volatile and non-volatile, removable and non-removable media implemented in any method or technology for storage of information such as computer-readable instructions, data structures, program modules or other data. For example, computer-readable storage media includes random access memory (RAM), read-only memory (ROM), erasable programmable read only memory (EPROM), electrically erasable programmable read only memory (EEPROM), flash memory or other solid state memory technology, CD-ROM, DVD or other optical storage, magnetic cassettes, magnetic tape, magnetic disk storage or other magnetic storage devices, or any other medium which can be used to store desired information and which can be accessed by the computing device 120.

As noted above, one type of program stored in the memory 126 is a pathway planning module. As an initial step of pathway planning, image data of a patient (typically in DCOMM format) from for example a CT image data set (or other imaging modality) is imported into the pathway planning module. Imaging may be done by CT imaging, magnetic resonance imaging (MRI), functional MRI, ultrasound imaging, X-ray, and/or any other imaging modalities.

The pathway planning module processes images of a patient and creates a three-dimensional model of a desired portion of the CT image, for example the lungs. To generate the 3D model, the pathway planning module employs segmentation, surface rendering, and/or volume rendering. Details of these processes and the pathway planning module can be found in commonly assigned U.S. patent Publication No. 2014/0281961, the entire contents of which are incorporated herein by reference. Such pathway planning modules permit the user to view individual slices of the CT image data set, and to identify one or more targets. These targets may be, for example, lesions or the location of a nerve which affects the actions of tissue where lung disease has rendered the lung function compromised or others. Having identified these targets, the pathway planning module enables the user to develop a plan to either achieve access to the target, for example by extending a biopsy or other tools through a natural orifice or an incision to be made by a clinician, or to pin-point the location and identify the coordinates of the target such that they can be employed by a treatment device 110, as will be described below. The pathway planning module guides a clinician through a series of steps to develop a pathway plan for later use for obtaining images with refined resolution. A clinician communicates with the pathway planning module via the display device 122 which displays interactive features to receive inputs from the clinician. The pathway planning module may be employed to further refine the resolution of one or more targets to identify and locate a nerve to be denervated. The term, clinician, includes doctor, surgeon, nurse, medical assistant, or any user of the pathway planning module involved in planning, performing, monitoring and/or supervising a medical procedure.

The network interface 128 enables other computing devices 120 and/or the treatment device 110 to communicate with each other through a wired and/or wireless network connection. In FIG. 1, the treatment device 110 may transmit or receive medical images, medical data, and control data with the computing device 120 via a wired connection. In a case where the network interface 128 connects to other computing devices 120 or the treatment device 110 wirelessly, the network interface 128 uses a frequency for communication, which is different from the frequencies that the treatment device 110 uses for treatment.

The input device 129 is used for inputting data or control information, such as setting values, text information, and/or controlling the treatment device 110. The input device 129 includes a keyboard, mouse, scanning devices, or other data input devices.

The treatment bed 130 receives the patient to be treated. The support 140 supports the treatment bed 130 and may have mechanical structures to make the treatment bed 130 movable horizontally and vertically. For example, when a patient lies down her body on the treatment board 130, the support 140 adjusts the height of the treatment board 130 and moves the treatment board 130 to and from the treatment device 110, so that a target of the lung to be treated is placed at an optimal height and under the treatment device 110 for treatment.

In embodiments, in case that the treatment device 110 is also used for imaging the lung to make a three dimensional model, the support 140 may move the treatment bed 130 in three transversal directions, namely, transversally, coronally, and sagittally. Or, the treatment device 110 may have imaging sensors that capture slices of image of the patient's body in the three directions without moving the patient 160.

The treatment bed 130 includes a field generator 135. The field generator 135 may be employed for a number of functions. The primary function is to enable the registration of the CT image data, and particularly the targets identified therein during the pathway planning steps, with the location of a patient 150 lying on the treatment bed 130. As will be appreciated, in instances where the imaging and treatment are performed on different machines, at different times, or at different locations, registration of the patient with the image data is important to ensure that treatment is occurring at the proper locations within the patient. Registration of the patient 150 with the image data may be undertaken in a variety of ways.

One methodology for registration is to traverse a probe with a sensor through two or three bifurcations of a patient's bronchial tree. The sensor may be placed for example on a bronchoscope. The sensor detects the electromagnetic field generated by the field generator 135, and outputs a signal representative of its location. This signal is used in combination with image registration software, to match bronchoscopic image data with an internal view of the 3D model generated in the pathway planning steps described above. A variety of factors are employed in the registration process and its details are described in greater detail in commonly assigned U.S. Pat. No. 8,218,846, the entirety of which is incorporated herein by reference. Once registered, the location of the patient within the electromagnetic field is known relative to the location of the target identified during pathway planning, and the coordinates of the target can be used to conduct treatment.

In embodiments, when respiratory movements of the patient 160 are to be monitored, the field generator 135 may be coupled with one or more sensors located on the patient 150 so that the patient's respiration and particularly the patient's movements can be monitored and accounted for during treatment. For example, movement tracking sensor 155 may be electromagnetically coupled with the treatment bed 130 or the field generator 135. When the patient 150 breathes in and out, air flows in and out of the lung so as to inflate or deflate the lung, respectively. The movement tracking sensor 155 also moves accordingly and senses changes in location with respect to the treatment bed 130. The movement tracking sensor 155 may be placed on at least two body parts to consider comparative movements of different body parts (e.g., the width and depth of the chest).

Since the movement tracking sensor 155 does not actually track the movement of the target nerve, a breathing model is selected to correlate the respiratory movement and the movement of the target nerve. In this way, movements of different body parts are considered and are registered to CT images so that the accurate location of the target nerve during denervation treatment may be identified.

In embodiments, the field generator 135 may cover the whole treatment bed 130 and may activate a portion of the field generator 135 so that only such portion can be monitored. The field generator 135 may generate a field other than the electromagnetic field, which can be used for monitoring a location of sensors located on the patient 150 and which is known to a person of ordinary skill in this area.

FIGS. 2A-2F show one of effective imaging modalities of identifying targets, i.e., computed tomographic (CT) technique. The use of CT images as diagnostic tools has become routine and CT results are frequently the primary source of information available to a clinician regarding the size and location of a target lesion, tumor, or other similar target of interest. CT images are typically obtained by digitally imaging a patient in slices in each of the transversal, coronal and sagittal directions. For example, FIG. 2A illustrates a slice of a CT image taken from the transversal direction. In other words, CT images are cross-sectional views taken at a plane perpendicular to the transversal direction or perpendicular to the spine of the patient as illustrated in FIG. 2B. FIG. 2C illustrates a slice of a CT image taken from the coronal direction. In other words, CT images are cross-sectional views taken at a plane perpendicular to the coronal direction as illustrated in FIG. 2D. FIG. 2E illustrates a slice of a CT image taken from the sagittal direction. In other words, CT images are cross-sectional views taken at a plane perpendicular to the sagittal direction as illustrated in FIG. 2F. A clinician may review the CT image data slice by slice from each direction when attempting to identify or locate a target, as described above during the pathway planning phase.

In embodiments, these slices of images captured in the three directions, i.e., transversal, coronal, and sagittal directions, are input to the computing device 120 which, in turn, generates a three dimensional model of the patient's lung. Generally, CT images include images of all organs inside of the patient's body. The computing device 120 processes the CT images so that images of most of organs are included in the three dimensional model. The three dimensional model may selectively show only the left and right lobes of the lung, bronchial trees, or the trachea. Nevertheless, two dimensional images (i.e., CT images) are used to see images as is taken.

Figure 3:
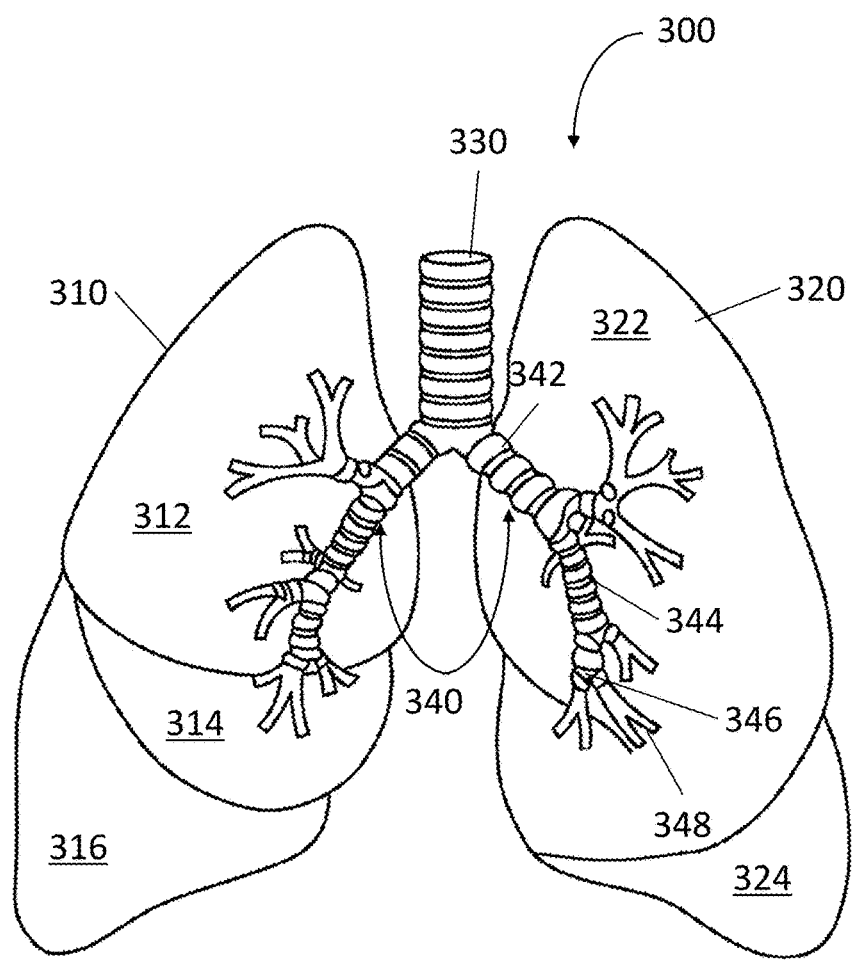
FIG. 3 is an anatomical illustration of a three dimensional model for a lung in accordance with an embodiment of the present disclosure.

FIG. 3 illustrates a three dimensional model 300 for a patent's bronchial trees and the trachea together with the lung according to an embodiment of the present disclosure.

The three dimensional model may include information of most of the organs so that a clinician may selectively see particular organs or portions of organs of interest as shown in FIG. 3. In this case, these selected organs are the lungs including right lobe 310, the left lobe 320, the trachea 330 and bronchial trees 340. The right lobe 310 has three sub-lobes, i.e., superior lobe 312, middle lobe 314, and inferior lobe 316, and the left lobe 320 has two sub-lobes, i.e., superior lobe 322 and inferior lobe 324.

The trachea 330 is a tube that connects the pharynx and larynx to the lung 310 and 320. At the lower end of the trachea 330, left or right primary bronchus 342 is divided. Secondary bronchus 344 also divides at the lower end of the primary bronchus 342. The circumference of the primary bronchus 342 is greater than that of the secondary bronchus 344. In the same manner, tertiary bronchus 346 divides at the lower end of the secondary bronchus 344 and terminal bronchiole 348 divides at the lower end of the tertiary bronchus 346. The primary bronchus 342, the secondary bronchus 344, and the tertiary bronchus 346 are supported by cartilaginous plates. However, when the size of the tertiary bronchus 346 becomes smaller and smaller, the cartilaginous plates disappear and outer wall is dominated by smooth muscle. The outer wall of the terminal bronchiole 348 is also dominated by smooth muscle.

A target nerve may exist on any bronchial trees, the primary bronchus 342, the secondary bronchus 344, the tertiary bronchus 346, and the terminal bronchioles 348. Effects of denervation of a target may be based on severity of symptoms or the location of the target nerve. If symptoms of the lung diseases are severe, plastic denervation may be performed, or if the symptoms are mild, elastic denervation may be performed. Plastic denervation wholly disables functions of the target nerve and elastic denervation partly disables the functions. If a target nerve is located on the primary bronchus 342, functions of nerves which are connected to and located below the target nerve, which is on the following secondary, tertiary, and terminal bronchial trees, may be disabled wholly or partly. In the same way, when a target nerve is located on the terminal bronchioles 348, only the functions of the target nerve is disabled wholly or partly but nerves connected to and located above the target nerve perform their functions well without being affected by the denervation.

Additionally, if symptoms of the lung diseases are severe, a treatment size may be greater than the size of the target nerve and, if not, the treatment size may be equal to or smaller than the size of the target nerve. Thus, the treatment size of the target nerve depends on severity of the symptoms of the lung disease, a location of the target nerve, and a size of the target nerve.

According to some embodiments, a further refinement for the slices of images is necessitated when a selected imaging modality does not give sufficient resolution to locate a target nerve. This may be particularly true when seeking to treat the tertiary bronchus 346 or the terminal bronchiole 348. In this case, another imaging modality may be used to provide further refined resolution of the slices of images so that target nerves can be identified and located.

In accordance with one embodiment, an ultrasound imaging modality may be employed to provide greater specificity and greater accuracy in identifying the target nerve's location in the patient 150. In one such embodiment, a radial ultrasound probe is employed following the pathway plan described above and images are taken of the pathway. These images may be registered to those of the CT image data and/or the 3D model to provide greater clarity with respect to the location of a target nerve. For example, this data may also be used diagnostically to help the clinician confirm that all likely candidates for targeting have been identified. As will be appreciated, other imaging modalities may be employed to enhance the first image data collected (e.g., the CT image data), these modalities includes various forms of ultrasound both internal and external to the patient, magnetic resonance imaging (MRI), fluoroscopy, and others without departing from the scope of the present disclosure.

Figure 4:
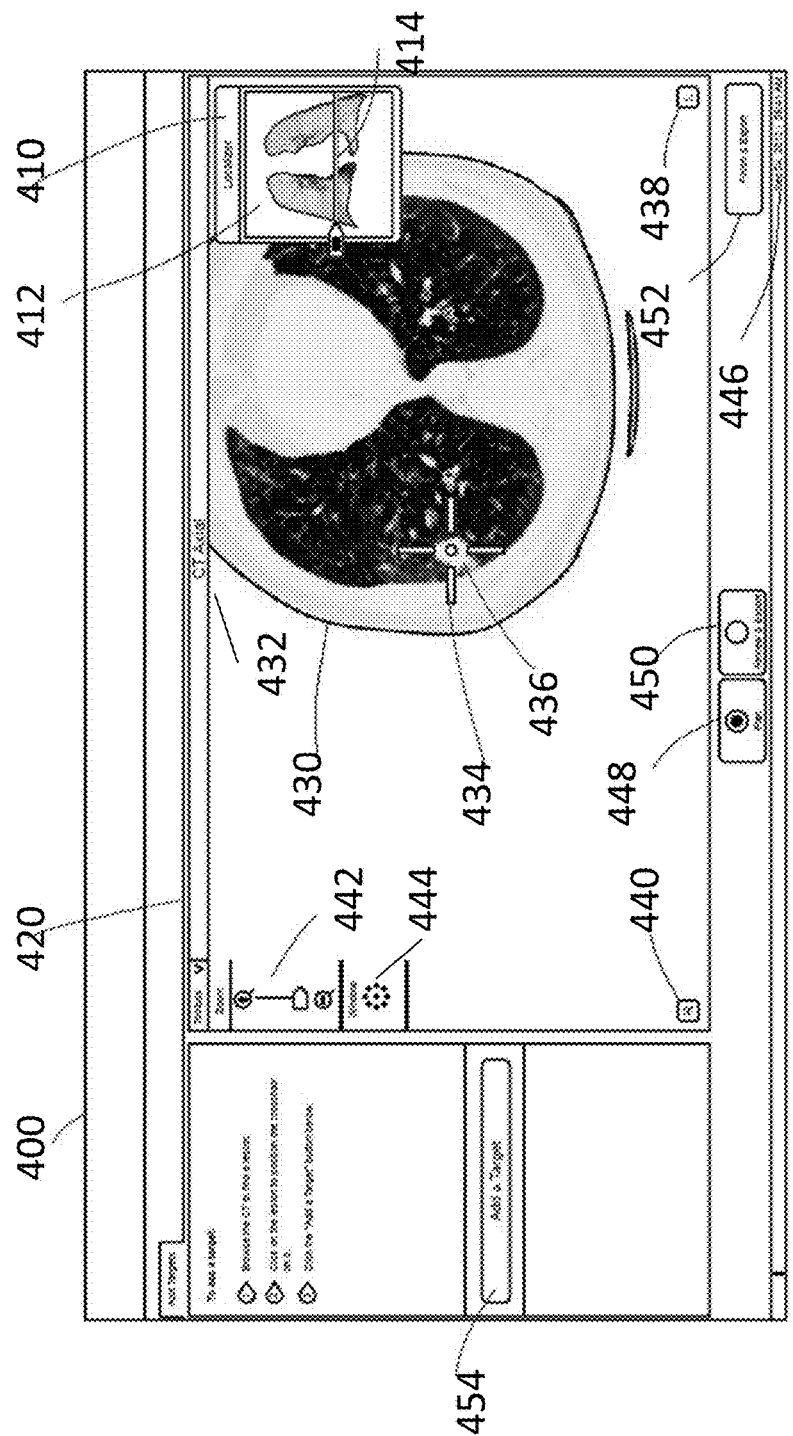
FIG. 4 is an illustration of a user interface for adding a target to a pathway plan in accordance with an embodiment of the present disclosure.

FIG. 4 illustrates a user interface 400 of the pathway planning module for adding a target and ultimately for developing a pathway plan in accordance with an embodiment of the present disclosure. If a clinician selects to create a new pathway plan, the user interface 400 is displayed on a display. The user interface 400 includes a localizer 410 and a main window 420.

The localizer 410 shows a view orthogonal to the main image of the screen, here the main view is the axial view, thus the localizer is in the coronal view showing the left and right lobes 412 of a patient's lung and a location bar 414. As depicted in FIG. 4, a clinician can move the location bar 414 vertically, which has the effect of changing the slice of the CT image the axial direction as shown in FIG. 2A, to scroll through the CT images taken at a plane perpendicular to the axial direction as shown in FIG. 2B. The clinician may also or alternatively scroll through the CT images of the patient's lungs via an input device such as a mouse wheel or other device without directly moving the location bar 414. When another direction is selected for display on the three dimensional model, for example, the coronal direction, the localizer 414 may display a coronal view of the organ requiring treatment (here shown as the lungs). The localizer 414 provides the clinician with a general reference for where the CT slice 430 the clinician is currently viewing is located in the organ being considered. The localizer 414 may also display one or more previously identified targets for the clinician's reference.

The main window 420 shows an image 430 which corresponds to a CT image taken at a plane where the location bar 414 is located in the left and right lobes 412. Title 432 indicates that the image 430 is a CT image taken in the direction of the transversal or axial direction. Date and time section 446 indicates the date and time when the CT image 430 was taken. Thus, a clinician can determine whether the image 430 was sufficiently recent for planning a pathway for a target. In case when the clinician determines that the image 430 is too outdated for the pathway planning, new images should be taken as shown in FIGS. 2A-2F for generation of a new 3D model and the pathway planning.

Target selection tools such as the cross hairs 434 helps the clinician to select a target 436. Direction indicators 438 and 440 indicate which direction is right and left. As shown in FIG. 4, the target is selected in the right lobe of the lung based on the direction indicators 438 and 440.

Zoom slider bar 442 is used to zoom in and out to see details of or general view of the image 430. For example, if the slier of the zoom slider bar 442 is close to zoom-out icon, a particular portion of the image 430 is reduced and, if the slider of the zoom slider bar 442 is close to zoom-in icon, the particular portion of the image 430 is enlarged. Window icon 444 may be used with the zoom slider bar 442 to refine a selection size of the target 436. When the target 436 is located by the target selection 434, the clinician may use the zoom slider bar 442 to zoom in the selected area and closely identify the target by resizing and/or relocating the target window using the window icon 444.

When the target 436 and its size are identified, the clinician clicks plan button 448 to make a pathway plan to the target. The pathway plan may be reviewed and exported by clicking review & click button 450. If the clinician determines that the pathway plan is acceptable, the pathway plan is finished and exported by clicking finish & export button 452. If there is more than one target, the clinician can add more target by clicking add a target button 454 and doing the same things as described above. Detailed methods for planning a pathway are described in commonly assigned U.S. Pat. No. 9,459,770, filed on Mar. 15, 2013, to Baker and U.S. patent application Ser. No. 14/821,912, filed on Aug. 10, 2015, to Bharadwaj, et al, as well as the references cited therein, all of which are incorporated by reference in the present disclosure.

FIG. 5A shows a planar view of bronchial trees of a three dimensional model or of the slices of images of the lung such as the bronchial trees of FIG. 3. Assuming a target area is located at the tip of the bottom left end of the terminal bronchiole of FIG. 5A, FIG. 5B illustrates a pathway from the target area of the three dimensional model, which corresponds to a portion of the lung displaying symptoms of the lung disease, to a second area of the three dimensional model, which corresponds to the trachea. FIG. 5C illustrates an ultrasound transducer inserted into the lungs of the patient to the target following the pathway of the three dimensional model. When the ultrasound transducer reaches the portion of the lung, the ultrasound transducer transmits ultrasounds and receives sound reflects so that the tissue in that area can be more clearly defined and ultimately one or more nerves to be denervated around the target can be located and identified. In this way, CT imaging modality and the ultrasound imaging modality give sufficient resolution to identify sufficiently accurate location of one or more nerves to be denervated in the patient's lung.

FIGS. 5D and 5E illustrate an extended working channel 510 including an ultrasound transducer 525 that is position at the distal end of the extended working channel 510. The clinician navigates a luminal network of the bronchial trees and the trachea by following a pathway plan as shown in FIG. 5C so that the ultrasound transducer 525 can reach the identified portion of the lung tissue.

FIG. 5E is an enlarged detail view of a circled area 530 of FIG. 5D. while the distal tip of the extended working channel 510 or the ultrasound transducer 525 is navigated through the luminal network toward the identified portion, the ultrasound transducer 525 may radiate ultrasound waves and receives reflects to capture images of the luminal network and the identified portion, which has a greater resolution than that of the slices of images. It is described in greater detail in commonly assigned U.S. Patent Publication No. 2014/0046315, the entirety of which is incorporated herein by reference.

Figure 6:
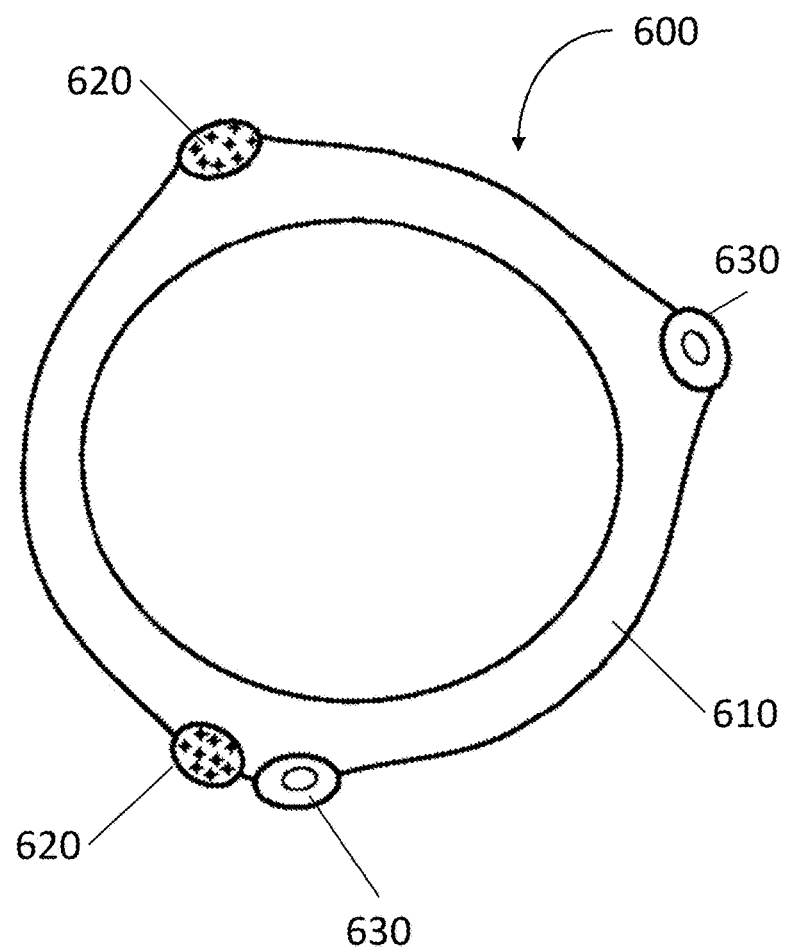
FIG. 6 is a cross-sectional view of the lung of FIG. 5A with respect to A-A direction.

FIG. 6 is a cross-sectional view 600 of the terminal bronchiole in the direction of A-A of FIG. 5A. The terminal bronchiole is surrounded by soft muscle 610. Nerves 620 and veins 630 are located on the soft muscle. The ultrasound imaging modality, as described above, provides a local view of the airways even out to the terminal bronchiole so that even the thin nerves 620 on the soft muscle 610 can be identified.

The lungs and tissue associated with the lungs are constantly in motion. As a result the nerves 620, move during a treatment because the thickness or size of the nerves 620 is relatively small compared to a movement of any patient's body part (e.g., the lung, diaphragm, or vascular tissue) or any operational movement of clinician (e.g., the treatment device 110 or the treatment bed 130). Thus, such movements should be compensated for to accurately identify, locate, and treat a target nerve.

The target nerve 620 may be cholinergic-parasympathetic nerve, which mediates contractions of muscle, or adrenergic-sympathetic nerve, which mediates relaxation. The target nerve 620 may also be a pre- or post-ganglionic nerve.

Figure 7:
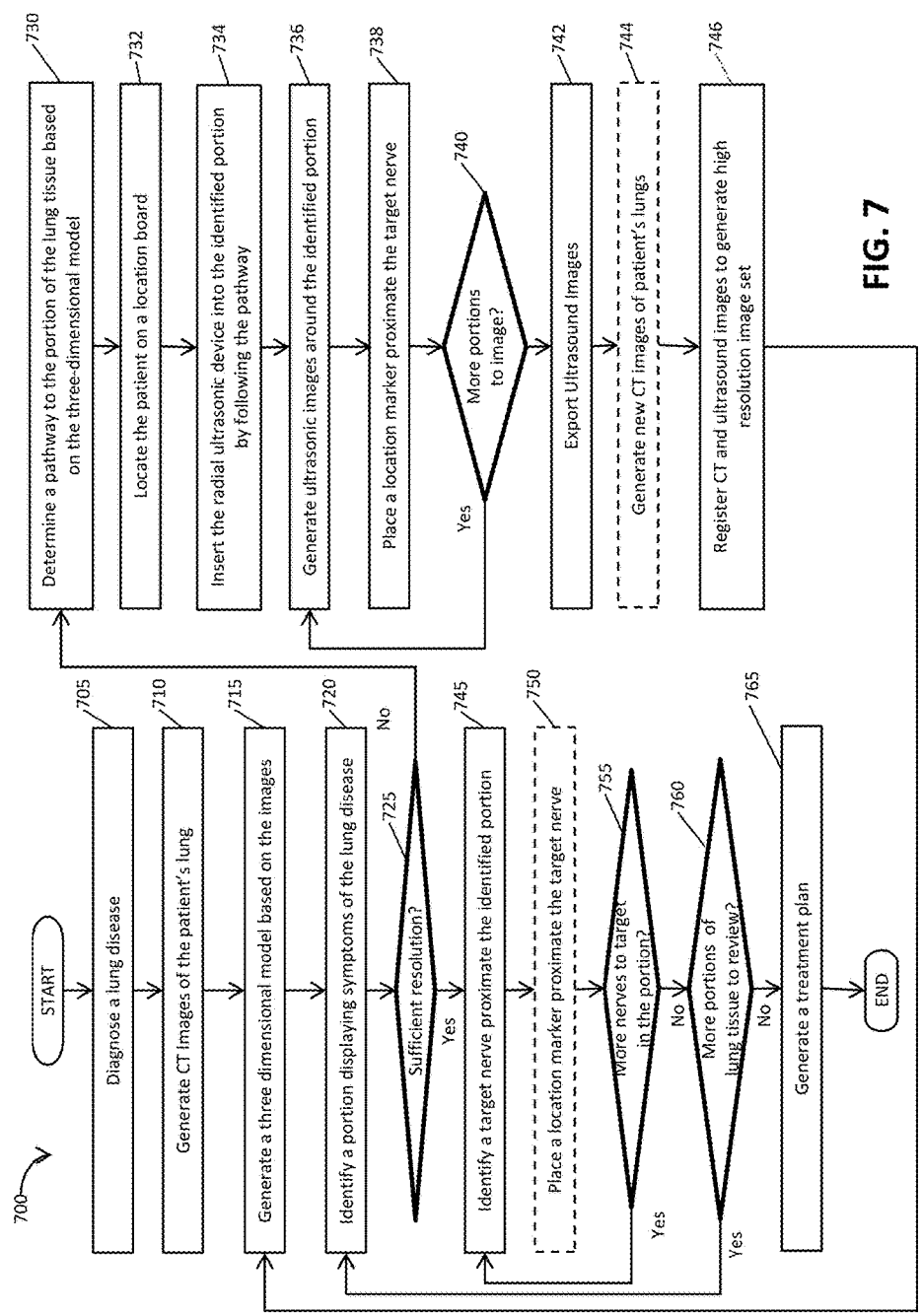
FIG. 7 is a flowchart of a method for generating a treatment plan to treat a lung disease in accordance with an embodiment of the present disclosure.

FIG. 7 shows a flowchart illustrating a method 700 for generating a treatment plan to treat a lung disease by denervation. The method 700 locates and identifies one or more targets and then generates a treatment plan for the targets. In step 705, a clinician diagnoses a lung disease by inspection, palpation, percussion, and/or auscultation.

After the lung disease is diagnosed, an imaging device takes images of the patient 150 using for example a MRI or CT imaging device in step 710. Typical MRI or CT imaging devices render images of the patient in three axes, i.e., transversal, coronal, and sagittal directions. In embodiments, the clinician may use imaging enhancing agents to fluorescently dye the lung before taking images so as to identify the location of the lung in either the images or under visualization. Some of the imaging enhancing agents may be transportable axonally anterogradely or retrogradely to help visualize the white matter track (axon) or gray matter nucleus in brain. In other words, the imaging enhancing agents may help to visualize nerves located in and around the bronchial tree. This may be provided to the patient even before the image of the lung is taken so that, when the images of the lung are taken, the fluorescent marker is depicted on the images clearly. Imaging enhancement agents may be fluorescent dye or FLUOROGOLD™. For example, FLUOROGOLD™ is a neuronal retrograde tracer which stains the dendrites of nerve completely. When FLUOROGOLD™ is injected the nerve becomes fluorescently dyed and as a result emits frequencies of fluorescent light when excited by a specific frequency of light. In this way, an imaging device or fluorescence microscopy detects the fluorescent light so that a clinician can differentiate the nerve from other organs with clarity. Other markers for identifying the location of nerve tissue may be employed by those of ordinary skill in the art without departing from the present disclosure.

These images are combined and processed to generate a three dimensional model of the bronchial tree of the patient's lung in step 715. Generally, the more images taken in each direction, the more refined model may be created. Nevertheless, at some point, more slice images do not help enhancing resolution of the three dimensional model due to limitations of the selected image modality. Thus, an optimum number of slice images is taken in each of the three directions and is pre-determined in consideration of the specification of the imaging modality and a required resolution.

In step 720, a clinician reviews the three dimensional model/and or the MRI or CT images to identify the portions of the lung suffering from disease and requiring treatment. This is a gross determination and focuses the clinician's attention on the appropriate portion of the lung, wherein identification of specific nerves will be targeted and treated as described in detail below.

In embodiments, the three dimensional model may have information of most of the internal organs and other physiology in or around the lung, for example, heart, ribs, spine, and lung, bronchial trees, and diaphragm. The clinician may see organs selectively and may rotate the three dimensional model around any direction so that the clinician can decide which way is a more suitable direction to avoid hard tissues such as bones while treating a target nerve. Depending on the resolution of the three dimensional model, nerves for treatment may be visible in the model and the clinician can use tools in the user interface to mark these nerves for targeted treatment. In such an embodiment, it may not be necessary to review the individual CT images.

In step 725, it is determined whether the three dimensional model and CT images have sufficient resolution to identify a target nerve proximate the identified portion of the lung. For example, if the identified portion of the lung for treatment is on a primary or secondary bronchial tree, then the three dimensional model and CT images may provide sufficient resolution to identify a target nerve. However, if the identified portion is on a tertiary or terminal bronchial tree, the three dimensional model and CT images may not provide sufficient resolution to do such.

When it is determined that the three dimensional model or CT images provides sufficient resolution, the clinician may identify a target nerve to be treated proximate the identified portion in step 748. The identification of a target refers to the placement of a target on the images and/or three dimensional model by the clinician. The target and specifically the coordinates of the target in the image and three dimensional model are used to direct the treatment device, as will be described in detail below.

In step 750, a location or fiducial marker may be optionally placed in the lung tissue proximate the target nerve. Generally, treatment of the target nerve takes place in a different time and space from identifying the target nerve. Thus, at a later check-up or another imaging of the lung for treatment, the clinicians may have to confirm the location of the target nerve. In this case, the location marker is used to guide the clinicians back to the same location which is proximate the portion of the lung displaying the symptoms of lung disease. The fiducial markers may also being employed in one or more registration process for treatment of the target nerve. In embodiments, a plurality of markers may be placed in the lung tissue so that, when the plurality of markers are imaged at a later time for treatment, a clinician may identify the size and depth of the target nerve based on the image showing topology of the plurality of markers.

In step 755, it is determined whether there are more nerves to target in the identified portion of the lung suffering from lung disease. When it is determined that there are more nerves to target in the identified portion in step 755, steps 748, 750, and 755 are repeated until there are no more nerves to target. If it is determined that there are no more nerves to target, in step 760, the clinician further determines whether there are more portions of the lung that displays symptoms of the lung disease, which is different from the portion of the lung identified in step 720. When there are more portions, the method returns to step 720 until there are no more portions that display the symptoms of the lung disease.

In step 725, when it is determined that the three dimensional model and the images do not provide sufficient resolution to identify a target nerve, another imaging modality may be necessary to generate further refined images to provide a sufficient resolution to identify a target nerve. In embodiments, a radial ultrasound imaging modality may provide such resolution of the identified portion of the lung. In order to obtain such refined images of the identified portion, the ultrasound imaging device is to be inserted into the identified portion. Here, the three dimensional model is used to determine which pathway the ultrasound imaging device is to follow to reach the identified portion of the lung. Such guidance is called as a pathway plan.

The pathway plan, as an option to obtain further refined images of the identified portion, is determined to guide a radial ultrasound transducer of the ultrasound imaging device to the identified portion in step 730. As described in patent application Ser. No. 13/838,805 which is incorporated by reference, the pathway plan is determined starting from the identified portion of the lung to a bodily opening such as mouth, nose, or incision.

In step 732, the patient is located on a location board and a clinician inserts the radial ultrasound transducer starting from the bodily opening and ending to the identified portion of the lung by following the pathway plan of the three dimensional model in step 734. The clinician may use the pathway planning module stored on the memory 126 of the computing device 120 of FIG. 1. The pathway planning module displays the three dimensional model on the display device 122 such that the clinician can confirm that the radial ultrasound transducer follows the pathway plan determined from the three dimensional model in an order reverse to the pathway plan, i.e., starting from a bodily opening to the identified portion of the lung.

When the radial ultrasound transducer reaches the identified portion of the lung, the radial ultrasound transducer transmits high frequency sound waves radially. The sound waves are reflected from body organs in which density changes. In step 736, the radial ultrasound transducer detects the sound reflects and also transmits the detected sound reflects to the radial ultrasound imaging device which then processes the sound reflects and generates images In embodiments, tissue spectroscopy based on near infrared, infra-red, or Raman light scattering, optical coherence tomography, confocal microendoscopy, or fluorescence microendoscopy may be employed to provide sufficient resolution of the identified portion of the lung. Further, FLUOROGOLD™ may also be used to spectroscopically confirm nerve location.

In step 738, the clinician may place a location marker near the areas imaged using the radial ultrasound. These location markers help to identify approximately the location of the target nerve for a later use. As in step 750, a plurality of location markers may be used to identify the location. The location markers may be placed at the same time while imaging is undertaken or as part of an iterative process where imaging and marker placement are taken alternatively, such that a marker is placed at each area where radial ultrasound imaging is undertaken. At a minimum location markers will be placed in and around the portions of the lung tissue suffering lung disease as previously identified in the CT images or three dimensional model.

The target may be one or more points along a nerve length, meaning that targets are located along and down the length of a nerve, on a single plane, e.g., circumference of a bronchial tree, or along and down the length of a nerve in a different plane with a different distance apart from each other.

In step 740, it is determined whether there are more portions of the lung tissue to image with radial ultrasound. When it is determined that there are more portions to image, steps 736 and 738 are repeated using the generated ultrasound images until there are no more portions require imaging. Once all the portions of the lungs are imaged using radial ultrasound, the radial ultrasound images are exported to the computing device 120 and stored in memory 126 at step 742.

At this point the clinician has a decision to make. The radial ultrasound images taken in step 736 provide greater localized detail than the original CT images taken in step 710. Thus the radial ultrasound images may be registered to and combined with CT images to generate a high resolution image set. The decision to be made is whether to generate a new CT image at step 744. The benefit is that by generating a new CT image, the fiducial markers which were placed in step 738 will now also be imaged and provide for greater ability to register and clearly identify the location of targets for both treatment planning and treatment of the patient. However, in some instances it may be sufficient to forego the second CT imaging step and simply register the ultrasound images generated in step 736 with the original CT images generated in step 710. Accordingly, whether using the original CT images from step 710 or newly generated CT images from step 744, the CT images and the ultrasound images are registered to one another and a high resolution image set is generated in step 746.

From step 746, the process loops back to step 715 where a three dimensional model is generated, but this time using the high resolution image set. This process continues through step 760, as described above, to identify the locations of target nerves in the high resolution image set, until it is determined that there are no more nerves and no more portions of the lung tissue to review in steps 755 and 760.

When it is determined that there are no more nerves to identify in step 755 and no more portions of the lung t review in step 760, a treatment plan is generated in step 765. The treatment plan includes information which is necessary to treat all the targets identified in the method. For example, the treatment plan may include the size, depth, and location of each target nerve. Based on the information of each target nerve, the treatment plan may further include operational information on how to treat each target. The operational information may include an amount of energy to be radiated, a treatment period, a treatment vector, and the number of treatments to denervate a target nerve. The treatment period is a period during which the treatment device is applying energy to the tissue. Radiation of an amount of energy at the treatment vector for the treatment period may be determined such that it is not likely to harm tissues other than the intended target. Here, the treatment vector may be an angle at which treating energy is radiated to the target nerve. When the size or depth of the target nerve is larger or deeper than a predetermined size or depth, multiple treatments may be necessary to fully treat the target nerve. Even though an individual treatment may not harm tissues other than the intended target nerve, multiple treatments in the same location may harm the tissues other than the intended target. Thus, the treatment vectors may include a series of angles in a case of multiple treatments so that treating energy is not radiated via only one angle during the multiple treatments. The treatment plan may be dependent upon the severity of the lung disease. During treatment of target nerves, some tissues, such as hard tissues or bones, may absorb or reflect the treating energy. Such absorption or reflection of treating energy may cause an ineffective treatment or result in harms to some tissues other than the target nerves. Thus the treatment plan must be developed to avoid, to the extent possible interference from these structures.

The three dimensional model may be utilized to determine a treatment vector. Since the three dimensional model has most of the organs and can be rotated in any direction, the clinician may determine a treatment vector by looking at organs selectively and rotating the three dimensional model in any directions. In embodiments, the three dimensional model may be used to automatically provide several treatment vectors for multiple unit operations for one target nerve. Once generated, this treatment plan can be exported to a memory device 126 or directly to the treatment device 110 for use in treatment of the patient.

In embodiments, neuro-functional imaging modality may be used to provide the sufficient resolution of the identified portion of the lung. The neuro-functional imaging modality generates images of white matter anterogradely or retrogradely along long tracks of nerves or axons and may be registered with the MRI or CT images. Clinicians may identify the size of target nerves and make a treatment plan including a treatment period and energy based on the size.

Figure 8:
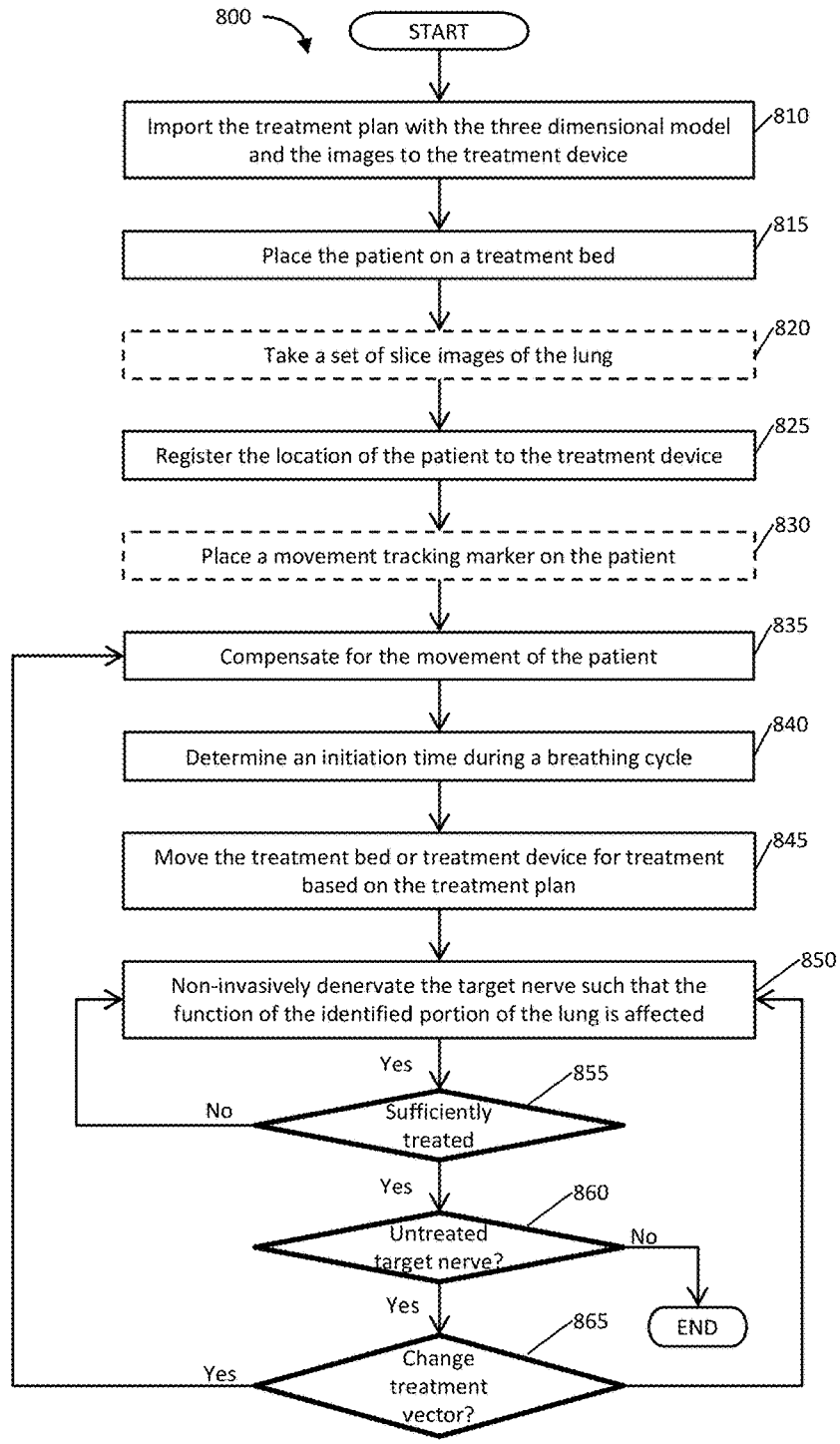
FIG. 8 is a flowchart of a method for treating the lung disease based on the treatment plan of FIG. 7 in accordance with an embodiment of the present disclosure.

FIG. 8 shows a flowchart illustrating a method 800 for treating target nerves. In 810, a clinician imports the treatment plan together with the three dimensional model, the images (including CT, ultrasound, and high resolution image set) to the treatment device. In step 815, the patient is placed on the treatment bed 130 of FIG. 1. In instances where the treatment device 110 is also an imaging device, in step 820, the clinician may performs a follow-up imaging of the patient's lung, this follow-up imaging may be used for registration purposes to determine the location of the patient 150 with respect to the treatment device. The clinician compares the new set of images with the previously taken images (e.g., the previous CT images or the enhanced resolution images) by looking at the location markers and registers the patient's location on the treatment device (i.e. the current image) with the prior images so that the treatment device can resolve the locations of target nerves in space with respect to the treatment bed and the patient 150. Step 820 is optional, there are other methods for registering the patient to the treatment device which are known to those of skill in the art including performing a bronchoscopy procedure with a sensor located in a bronchoscope to sense the electromagnetic filed emanating from field generator 135 of FIG. 1. The generated field is sensed by the sensor in the bronchoscope (not shown) so that the relative location of the sensor with respect to the patient and the treatment bed can be registered to the CT or enhanced resolution images. Here, the field generated by the field generator may be an electromagnetic field or may be other field that a person of ordinary skill in the art can implement so that a sensor can sense its location with respect to the treatment bed. In this way, the patient's location in space may be compensated for so that the treatment device can identify and verify the location of target nerves within the treatment device. Regardless of whether additional images are taken, in step 825, location of the patient in space on the treatment device 110 is registered to the treatment plan.

In step 830, one or more movement tracking sensors may be optionally placed on the patient to track the movement of the patient. The movement tracking sensors may be a sensor that can sense the field generated by the field generator 135. While the patient is placed on the treatment bed, the patient's lung moves due to respiration, movement of other organs such as diaphragm, or movement of the patient. Such movements should be considered and compensated before actual treatment begins. The movement tracking sensor may be a fiducial marker, location sensor, or beacon. The movements of the lung may be caused by respiratory movement, cardiac motion, and/or movement of the patient. The movement tracking marker may be electromagnetically coupled with the treatment bed so that movement of the patient with respect to the treatment board may be recorded.

In a case when the movement tracking sensor may be placed on the patient's body, more than one movement tracking sensor may be placed to find a breathing model which fits to the patient's breathing pattern and the lung movement. The breathing model shows relationship between movement of the lung and the patient's breathing pattern. Accurate estimation of a tertiary or terminal bronchus tree while the patient is breathing may not be easily obtained by a generic breathing model because breathing causes the lungs to move cyclically, meaning that the lung movement varies by amplitude and direction during the breathing cycle from 5 mm to 30 mm depending on such breathing characteristics as patient size, age, altitude, health, etc. U.S. Patent Publication No. 2009/0156951, entirety of which is incorporated by reference herein, describes a method to build a dynamic breathing model that can be used to accurately estimate movements of a small bronchial tree during a patient's breathing cycle.

Based on the breathing model, the clinician may estimate movement of the lung while patient is breathing. Since inhalation enlarges the chest, meaning that depth and width of the chest increase and exhalation deflates the chest, at least two movement tracking sensors are necessary to track changes in depth and width of the chest with reference to the treatment bed, one for depth and the other one for width.

Outputs of the movement tracking sensor is then transmitted to the treatment device. In step 835, the treatment device compensates the movement of the patient so that the treatment device may identify and locate the target nerve with respect to the treatment bed during a breathing cycle.

In embodiments, when the three dimensional model has pertinent information for treatment, the movement information may be displayed in the three dimensional model to assist the clinician in evaluating the treatment. In this case, the three dimensional model may be used throughout the end of the treatment for target nerves.

In step 840, the clinician can determine an initiation time for starting treatment during a breathing cycle. The treatment time included in the treatment plan starts from the initiation time. The target nerve of the lung moves the least starting from the initiation time for the operation period. The treatment period may be less than or equal to a period from a time when the patient is close to complete exhalation to a time when the patient is close to start inhalation or a period from a time when the patient is close to complete inhalation to a time when the patient is close to start exhalation. The treatment period may be a period while the patient holds a breath. If the treatment period determined in the treatment plan method 700 is larger than a period during which the lung moves the least, a number of treatments may be employed and, and the treatment vector may be adjusted based on the breathing model or pattern of the patient so that the adjusted operation information can apply to treating the patient.

In step 845, the treatment bed or the treatment device moves so that treatment can be performed according to the treatment plan. For example, if the location of a target nerve is in the superior lobe of the right lung, the treatment bed may move in the transversal direction so that the target nerve is under the treatment device. Or if the treatment angle for a target nerve is at an angle of 30 degree from the right hand side, the treatment device may rotate around the transversal direction so that the treatment device can treat the target nerve at that angle. While doing this, the clinician should verify and confirm that the registered location of the target in the treatment device matches the actual location of the target with respect to the treatment bed.

In step 850, denervation treatment is performed starting from the initiation time for the operation period such that the function of the identified target nerve of the lung is affected. The clinician may use SBRT to radiate stereotactic radiation from outside of the patient's body to denervate the target nerve at an angle defined in the operation vector. Or any other non-invasive treatment technique may be employed. Such treatment may be plastic or elastic denervation based on the severity of the lung disease.

In step 855, it is determined whether the target nerve is sufficiently treated. Determination may be performed based on real time imaging of the target nerve, or based on a calculation involving the target treatment volume, the amount of energy applied, and the duration of the treatment. If the target nerve is not sufficiently treated, another denervation process is performed until the target nerve is sufficiently treated. In this case, the treatment plan for the target nerve may also be adjusted so that consecutive treatments may not harm tissues other than the target nerve by changing angles listed in the operation vector, amount of energy, and/or the operation period included in the treatment plan. Here, the treatment may be used in conjunction with medical treatment (e.g., SPIRIVA® or lung function medications) to accelerate effects of the treatment or to compensate for lack of medical compliance.

If the target nerve is sufficiently treated, the clinician determines whether there are untreated target nerves in the treatment plan in step 860. If it is determined that there are no more target nerves in the treatment plan in step 860, treatments for all of the target nerves are completed. If there is an untreated target nerve, it is further determined whether or not changing treatment vector for another target nerve is required in step 865. This may happen when the new target nerve is in a location different from the previously treated target nerve or when the new target is treated at an angle different from that of the previously treated target nerve. If that is required, the treatment method returns to step 835 to compensate the movement of the patient because a different portion of the lung including the new target nerve may move differently from the portion of the lung including the previous target nerve. If not required, the treatment method returns to step 850 to treat the new target nerve non-invasively.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method for treating a lung disease, the method comprising:
    capturing a first set of images of at least a portion of a lung displaying symptoms of a lung disease;
    generating a first three dimensional model from the first set of images;
    locating a target nerve proximate at least the portion of the lung displaying symptoms of the lung disease;
    generating a treatment plan to treat the target nerve, the treatment plan including a treatment vector, the treatment vector including an angle at which energy is radiated to the target nerve, wherein, generating the treatment plan includes:
        selecting a second set of images from the first set of images including at least the portion of the lung displaying symptoms of the lung disease;
        sensing a location of an imaging device by a tracking sensor attached on the imaging device;
        navigating the imaging device inside a luminal network of the lung to at least the portion of the lung displaying symptoms of the lung disease based on the sensed location, wherein the imaging device generates enhanced images at the sensed location;
        combining the enhanced images with the second set of images to generate high resolution images corresponding to the sensed location, wherein a resolution of the high resolution images is higher than a resolution of the first set of images; and
        generating a second three dimensional model using the high resolution images; and
    non-invasively denervating the target nerve of a patient, by application of energy from outside of a body of the patient, based on the treatment plan such that a function of the portion of the lung is affected, including generating a breathing model for the patient, and compensating for a movement of the target nerve based on the breathing model during denervation.

2. The method according to claim 1, wherein the treatment plan further includes one or more of a treatment size, a nerve location, an amount of energy, or a treatment period.

3. The method according to claim 2, wherein, when the treatment plan includes the treatment size, the treatment size is calculated based on one or more of severity of the symptoms of the lung disease, a location of the target nerve, a size of the target nerve, and whether the denervation is to be temporary or permanent.

4. The method according to claim 2, wherein, when the treatment plan includes the amount of energy and the treatment period, non-invasively denervating the target nerve includes radiating the amount of energy to the target nerve for the treatment period.

5. The method according to claim 3, wherein the treatment plan further includes an initiation time to start denervating the target nerve during a breathing cycle of the patient.

6. The method according to claim 5 wherein the initiation time is a time when the target nerve moves the least during the breathing cycle.

7. The method according to claim 5, wherein the treatment period is a period from a time when the patient has completed inhalation to a time when the patient starts exhalation.

8. The method according to claim 5, wherein the treatment period is a period from a time when the patient has completed exhalation to a time when the patient starts inhalation.

9. The method according to claim 5, wherein the treatment period is a period while the patient holds a breath.

10. The method of claim 2, wherein the treatment period includes a plurality of treatments until the nerve has been radiated with the amount of energy of the treatment plan, the plurality of treatments including a plurality of treatment vectors, the plurality of treatment vectors including a plurality of angles.

11. The method according to claim 1, wherein compensating for the movement of the target nerve includes compensating for respiratory movement, cardiac motion, and movement of the patient.

12. The method according to claim 1, wherein generating the breathing model includes:
    locating the patient on a treatment bed; and
    placing a movement tracking sensor on the patient to monitor movement of the patient with respect to the treatment bed during a breathing cycle of the patient, wherein the breathing model is based on the movement of the movement tracking sensor during the breathing cycle of the patient.

13. The method according to claim 1, wherein the first three dimensional model is generated from the first set of images captured by one or more imaging devices selected from the group consisting of a computed tomography (CT), magnetic resonance imaging (MRI), and an ultrasound imaging device.

14. The method of claim 1, wherein the enhanced images are taken by one or more imaging devices selected from the group consisting of ultrasound imaging, tissue spectroscopy, optical coherence tomography, confocal microendoscopy, and fluorescence microendoscopy.

15. The method of claim 1, further comprising:
   determining a pathway plan for the portion of the lung based on the first three dimensional model and the first set of images,
   wherein navigating the imaging device includes:
      inserting the imaging device into the lung following the pathway plan; and
      imaging, by the imaging device, at least the portion of the lung displaying symptoms of the lung disease to generate the enhanced images.

16. The method of claim 15, further comprising placing one or more fiducial markers proximate at least the portion of the lung.

17. The method according to claim 16, wherein the one or more fiducial markers enable combination of the enhanced images and the second set of images.

18. The method of claim 1, wherein the target nerve for denervation is identified based on the first set of images or the high resolution images.

19. The method according to claim 1, further comprising employing a fluorescent marker to mark the target nerve prior to capturing the first set of images.

20. The method according to claim 1, wherein non-invasively denervating the target nerve includes:
   placing the patient on a treatment bed; and
   applying energy from outside of the body of the patient to the target nerve based on the treatment plan.

* * * * *